(12) United States Patent
Migliazza et al.

(10) Patent No.: US 9,326,858 B2
(45) Date of Patent: May 3, 2016

(54) FLEXIBLE ANNULOPLASTY RING

(71) Applicant: Edwards Lifesciences Corporation, Irvine, CA (US)

(72) Inventors: John F. Migliazza, Belmont Shore, CA (US); Bob Crockett, San Luis Obispo, CA (US); Tim Abram, San Luis Obispo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/759,928

(22) Filed: Feb. 5, 2013

(65) Prior Publication Data

US 2013/0211512 A1 Aug. 15, 2013

Related U.S. Application Data

(63) Continuation of application No. 13/216,472, filed on Aug. 24, 2011.

(60) Provisional application No. 61/376,578, filed on Aug. 24, 2010.

(51) Int. Cl.
*A61F 2/24* (2006.01)

(52) U.S. Cl.
CPC ............ *A61F 2/2448* (2013.01); *A61F 2/2466* (2013.01); *A61F 2250/0018* (2013.01)

(58) Field of Classification Search
USPC .................. 623/2.36–2.41; 600/37; 606/139, 606/151–158
See application file for complete search history.

(56) References Cited

U.S. PATENT DOCUMENTS 3,656,185 A 4/1972 Carpentier
4,055,861 A 11/1977 Carpentier et al.
(Continued)

FOREIGN PATENT DOCUMENTS

EP 0338994 A1 10/1989
EP 0860151 A1 8/1998
(Continued)

OTHER PUBLICATIONS

Adams, David, et al., "Large Annuloplasty Rings Facilitate Mitral Valve Repair in Barlow's Disease," Society of Thoracic Surgeons 42nd Annual Meeting, Jan. 30-Feb. 1, 2006.
(Continued)

*Primary Examiner* — Yashita Sharma
(74) *Attorney, Agent, or Firm* — Guy Cumberbatch; AnneMarie Kaiser; Pui Tong Ho

(57) ABSTRACT

An annuloplasty repair segment for heart valve annulus repair. In one embodiment a multi-stranded cable replaces solid core wire for both the tricuspid and mitral valves. Cable allows for greater deployment flexibility for minimally-invasive surgical (MIS) implant, while still maintaining the required strength and similar tensile properties of solid-core wire. In addition, selective placement of point-welds or other such control points locally control other parameters such as the amount and direction of displacement as the ring undergoes external loading. Cable with well-placed control points result in a MIS annuloplasty ring with sufficient flexibility in the x-y plane to allow a surgeon to squeeze the ring into a small incision, such as for example 1 cm×1 cm, while maintaining structural rigidity under forces exerted on the implanted ring by the cardiac cycle and allowing for asymmetrical deflection to be designed into the product.

22 Claims, 11 Drawing Sheets

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,275,469 A | 6/1981 | Gabbay |
| 4,602,911 A | 7/1986 | Ahmadi et al. |
| 4,790,844 A | 12/1988 | Ovil |
| 4,917,097 A | 4/1990 | Proudian et al. |
| 4,917,698 A | 4/1990 | Carpentier et al. |
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,397,348 A | 3/1995 | Campbell et al. |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,674,279 A | 10/1997 | Wright et al. |
| 5,716,397 A | 2/1998 | Myers |
| 5,728,064 A | 3/1998 | Burns et al. |
| 5,733,331 A | 3/1998 | Peredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,972,030 A | 10/1999 | Garrison et al. |
| 5,990,378 A * | 11/1999 | Ellis .......................... 623/11.11 |
| 6,010,531 A | 1/2000 | Donlon et al. |
| 6,019,739 A | 2/2000 | Rhee et al. |
| 6,024,918 A | 2/2000 | Hendriks et al. |
| 6,042,554 A | 3/2000 | Rosenman et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,348,068 B1 | 2/2002 | Campbell et al. |
| 6,368,348 B1 | 4/2002 | Gabbay |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,524,338 B1 | 2/2003 | Gundry |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,790,231 B2 | 9/2004 | Liddicoat et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,824,553 B1 * | 11/2004 | Samson et al. ................. 606/192 |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,962,605 B2 | 11/2005 | Cosgrove et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,361,190 B2 | 4/2008 | Shaoulian et al. |
| 7,452,376 B2 | 11/2008 | Lim et al. |
| 7,527,647 B2 | 5/2009 | Spence |
| 7,608,103 B2 | 10/2009 | McCarthy |
| 7,655,040 B2 | 2/2010 | Douk et al. |
| 7,699,892 B2 | 4/2010 | Rafiee et al. |
| 7,959,673 B2 | 6/2011 | Carpentier et al. |
| 7,993,395 B2 | 8/2011 | Vanermen et al. |
| 8,034,103 B2 | 10/2011 | Burriesci et al. |
| 8,123,802 B2 | 2/2012 | Kron et al. |
| 8,460,173 B2 | 6/2013 | Schweich, Jr. et al. |
| 8,535,374 B2 | 9/2013 | Redmond et al. |
| 8,591,576 B2 | 11/2013 | Hasenkam et al. |
| 8,734,507 B2 | 5/2014 | Keranen |
| 8,764,821 B2 | 7/2014 | Carpentier et al. |
| 2001/0034551 A1 | 10/2001 | Cox |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |

(56) References Cited

U.S. PATENT DOCUMENTS

| | | |
|---|---|---|
| 2005/0070999 A1 | 3/2005 | Spence |
| 2005/0075727 A1 | 4/2005 | Wheatley |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0009798 A1* | 1/2006 | Callister et al. ............... 606/200 |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0129236 A1 | 6/2006 | McCarthy |
| 2006/0149368 A1 | 7/2006 | Spence |
| 2006/0184241 A1 | 8/2006 | Marquez |
| 2006/0195183 A1 | 8/2006 | Navia et al. |
| 2006/0206203 A1 | 9/2006 | Yang et al. |
| 2006/0247491 A1* | 11/2006 | Vidlund et al. ................ 600/37 |
| 2006/0259135 A1 | 11/2006 | Navia et al. |
| 2007/0027533 A1 | 2/2007 | Douk |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0162112 A1 | 7/2007 | Burriesci et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0043381 A1 | 2/2009 | Macoviak et al. |
| 2009/0054982 A1* | 2/2009 | Cimino ....................... 623/13.19 |
| 2009/0177276 A1 | 7/2009 | Carpentier et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0287303 A1 | 11/2009 | Carpentier |
| 2010/0161047 A1 | 6/2010 | Cabiri |
| 2010/0211166 A1 | 8/2010 | Miller et al. |
| 2011/0166649 A1 | 7/2011 | Gross et al. |
| 2012/0078359 A1 | 3/2012 | Li et al. |
| 2012/0136436 A1* | 5/2012 | Cabiri et al. ................. 623/2.37 |
| 2012/0310330 A1 | 12/2012 | Buchbinder et al. |

FOREIGN PATENT DOCUMENTS

| | | |
|---|---|---|
| EP | 1034753 A1 | 9/2000 |
| WO | 9742871 A1 | 11/1997 |
| WO | 98/14138 A1 | 4/1998 |
| WO | 99/49816 A1 | 10/1999 |
| WO | 01/08608 A1 | 2/2001 |
| WO | 2005/004753 A1 | 1/2005 |
| WO | 2005/034813 A2 | 4/2005 |
| WO | 2008/063537 A2 | 5/2008 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, et al., Surgical Alternatives for Heart Failure, The Journal of Heart and Lung Transplantation, vol. 20, No. 7, pp. 729-733, 2001.

Bolling, Mitral Valve Reconstruction in the Patient With Heart Failure, Heart Failure Reviews, 6, pp. 177-185, 2001.

Caleya, et al., "Fracture of Carpentier's Ring in a Patient with Tricuspid Annuloplasty". Thoracic Cardiovascular Surgeon. vol. 31. pp. 175-176. 1983.

Carpentier, et al. "The 'Physio-Ring': An Advanced Concept in Mitral Valve Annuloplasty," Society of Thoracic Surgeons 31st Annual meeting, Jan. 30-Feb. 2, 1995.

Carpentier, et al., "Reconstructive Valve Surgery" Chapters 17-19, ISBN No. 978-0/7216-9168-8, Sanders Elsevier Publishing, Maryland Heights, Missouri, 2010.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., "Effect of Papillary muscle Position on Mitral Valve Function: Relationship to Homografts," The Society of Thoracic Surgeons, pp. 5155-5161, 1998.

Cosgrove, et al., "Initial Experience with the Cosgrove-Edwards Annuloplasty System," The Annals of Thoracic Surgery. vol. 60. pp. 499-504, 1995.

Cosgrove-Edwards, "Annuloplasty System," Edwards Lifesciences Corporation, 2000.

D.C. Miller, IMR Redux—To Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Galinanes, et al., "Fracture of the Carpentier-Edwards Ring in Tricuspid Position: A Report of Three Cases," The Annals of Thoracic Surgery, vol. 42, pp. 74-76, 1986.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Navia, Jose Luis., "Minimally Invasive Mitral Valve Surgery," Department of Thoracic and Cardiovascular Surgery, The Cleveland Clinic Foundation, 2001.

Salgo, et al., Effect of Annular Shape on Leaflet Curvature in Reducing Mitral Leaflet, American Heart Association, Circulation 2002; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association © 2005; ISSN: 1524-4539.

* cited by examiner

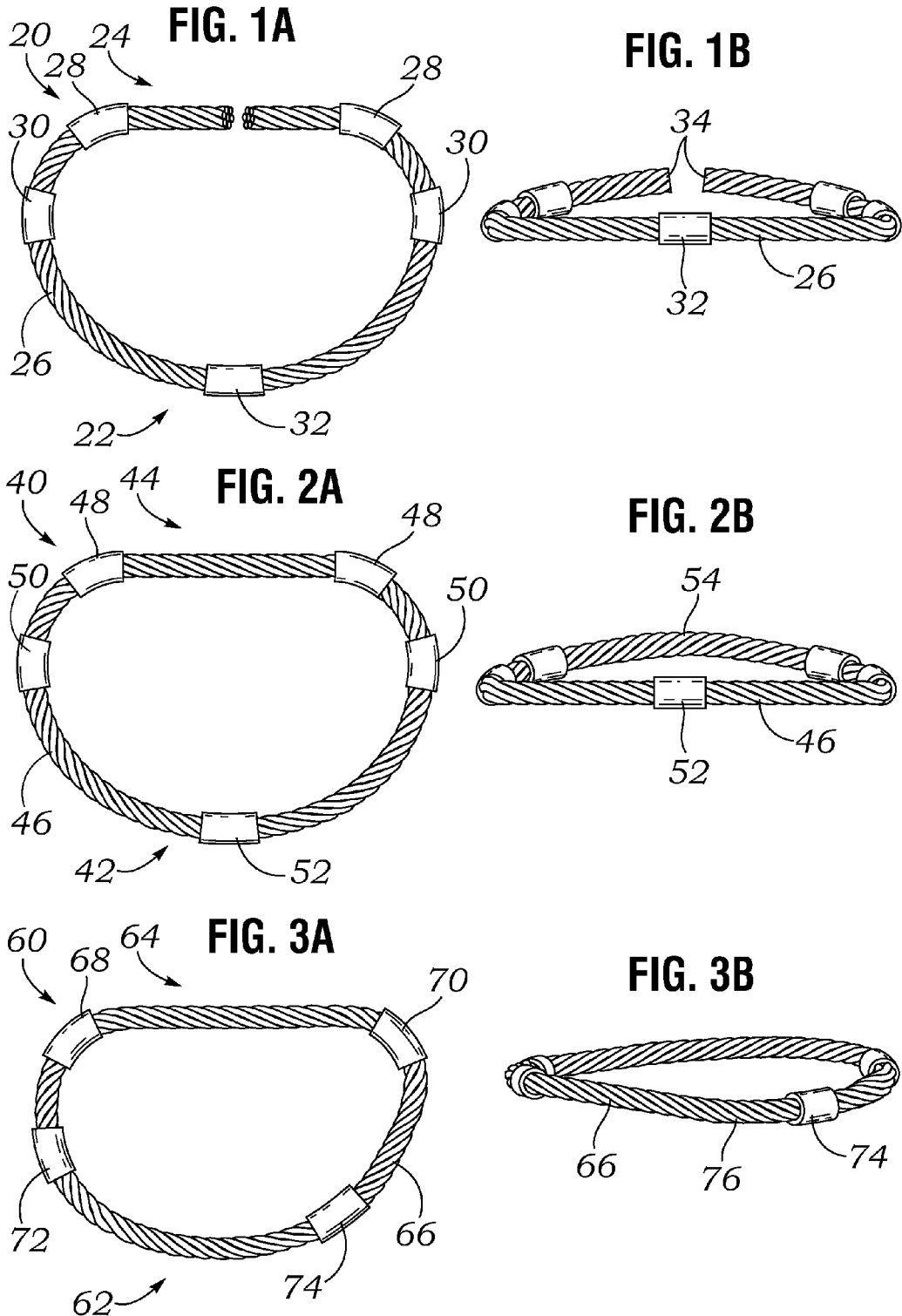

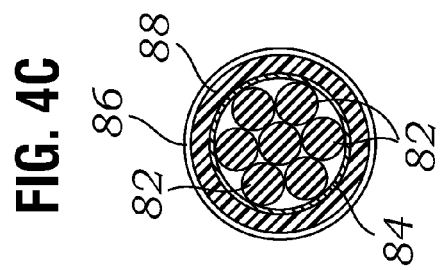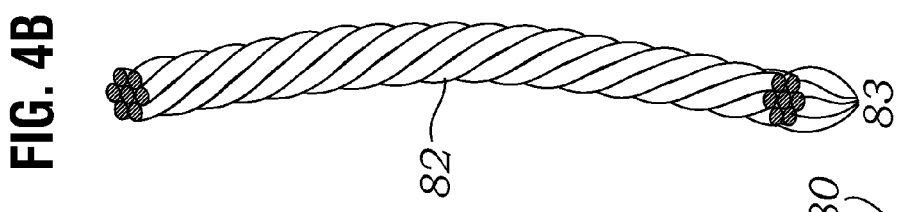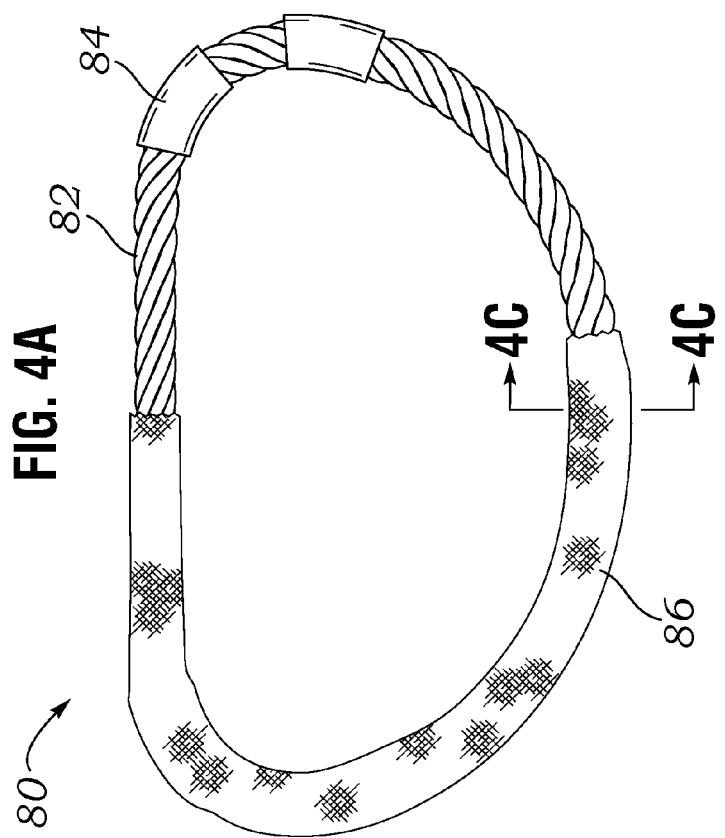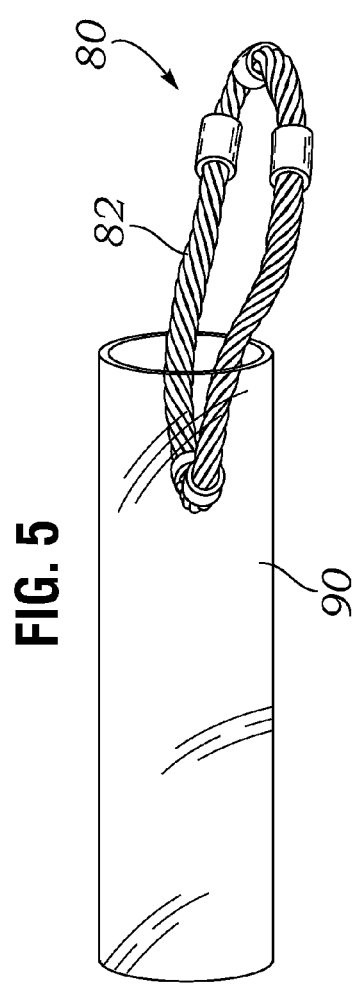

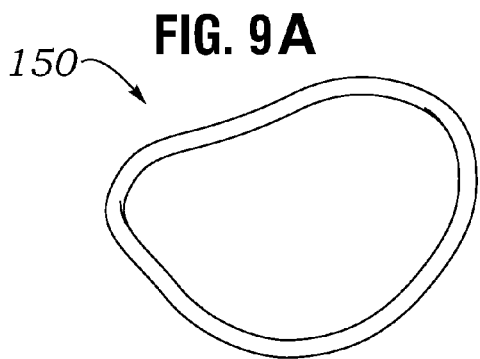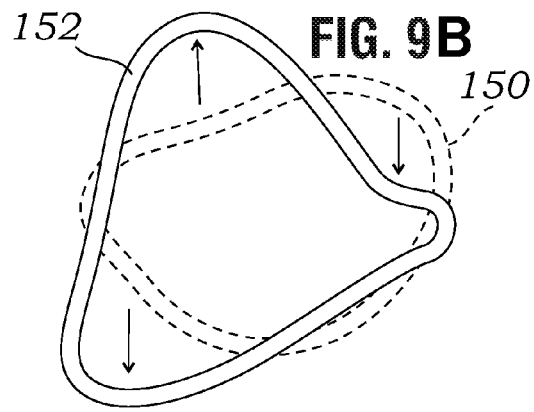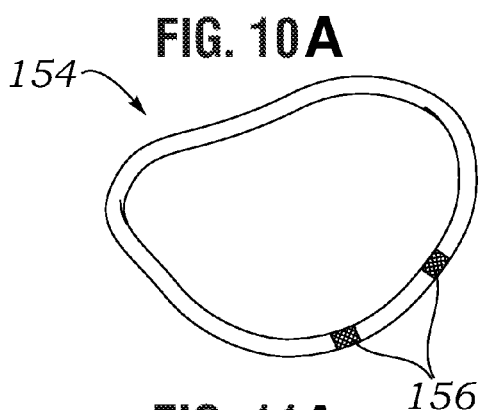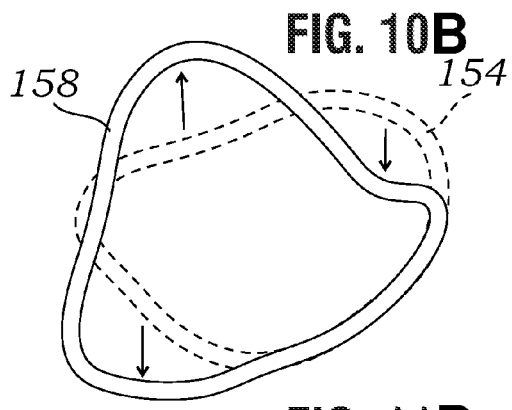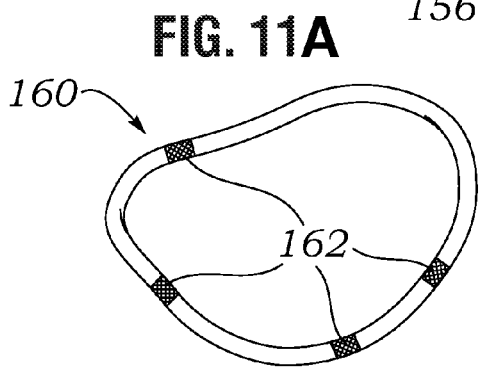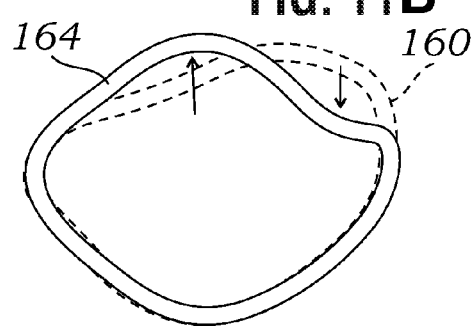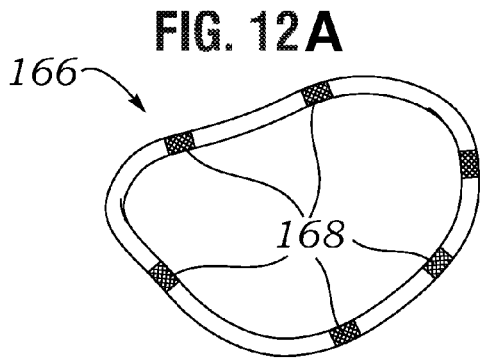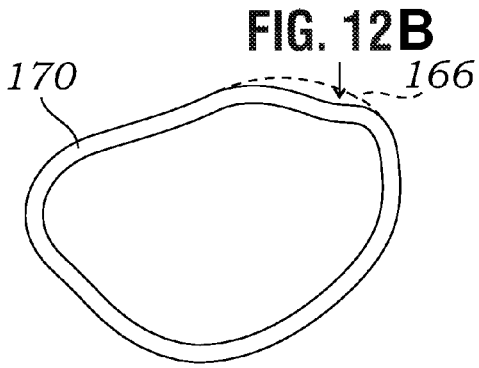

 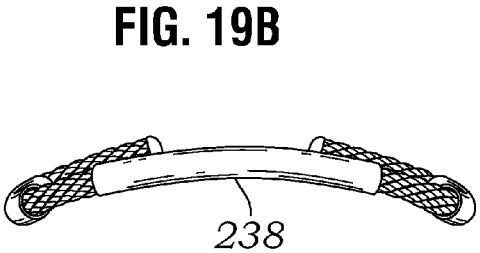
FIG. 19A  FIG. 19B
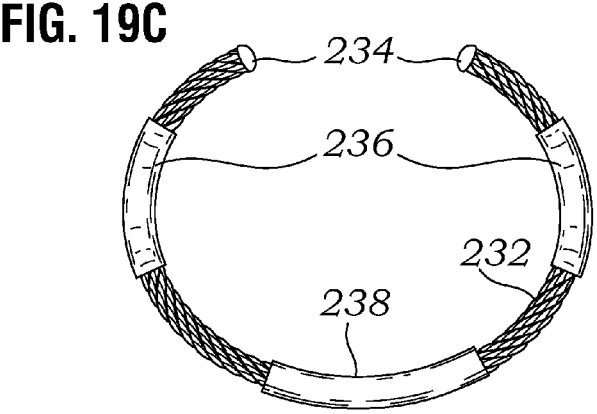
FIG. 19C
 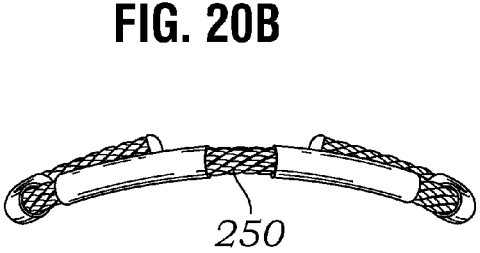
FIG. 20A  FIG. 20B
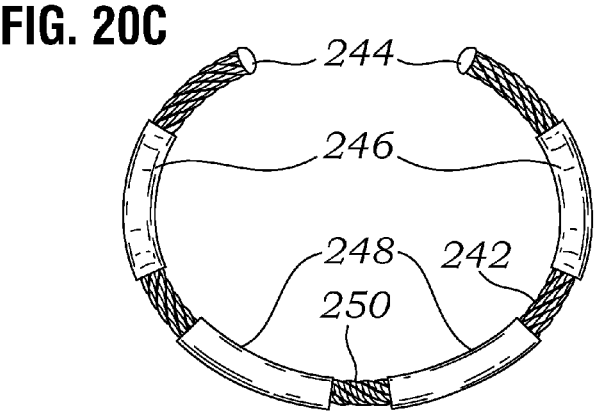
FIG. 20C

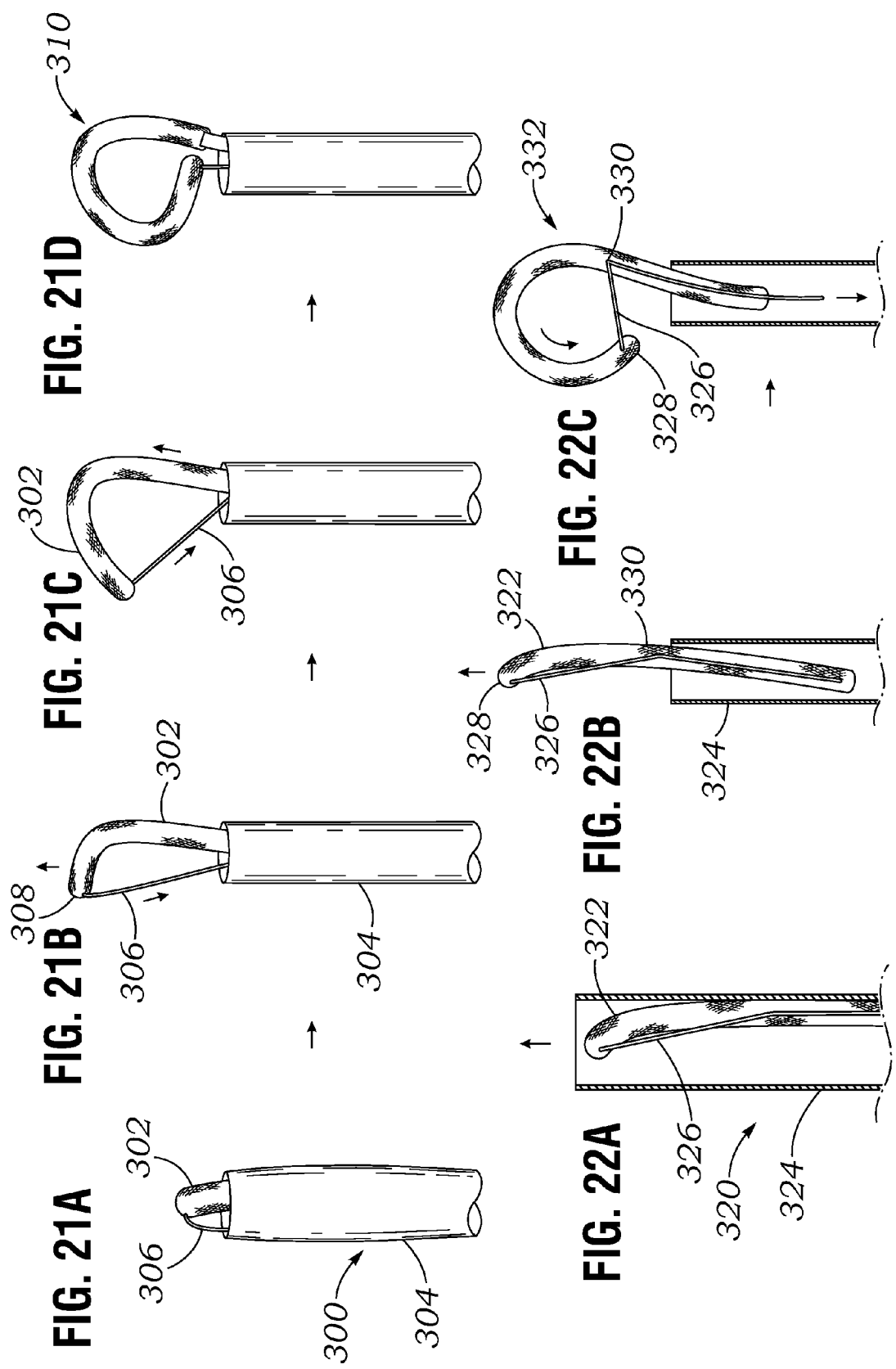

FLEXIBLE ANNULOPLASTY RING

RELATED APPLICATIONS

The present application is a continuation of U.S. patent application Ser. No. 13/216,472, filed Aug. 24, 2011, which claims priority under 35 U.S.C. §119 to U.S. Provisional Application Ser. No. 61/376,578, filed Aug. 24, 2010.

FIELD OF THE INVENTION

The present invention relates generally to cardiac implants and particularly to flexible annuloplasty rings especially for use in non-traditional surgeries.

BACKGROUND OF THE INVENTION

Prosthetic annuloplasty rings are used to repair or reconstruct damaged or diseased heart valve annuluses. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

As an alternative to valve replacement, various valve repair techniques have been used including quadrangular segmental resection of a diseased posterior leaflet, transposition of posterior leaflet chordae to the anterior leaflet, valvuloplasty with plication and direct suturing of the native valve, substitution, reattachment or shortening of chordae tendinae, and annuloplasty in which the effective size of the valve annulus is contracted by attaching a prosthetic annuloplasty ring to the endocardial surface of the heart around the valve annulus. An annuloplasty ring is designed to support the functional changes that occur during the cardiac cycle: maintaining coaptation and valve integrity to prevent reverse flow while permitting good hemodynamics during forward flow. The annuloplasty techniques may be used in conjunction with other repair techniques. The rings either partially or completely encircle the valve, and may be rigid, flexible, or selectively flexible.

Although mitral valve repair and replacement can successfully treat many patients with mitral valve insufficiency, techniques currently in use are attended by significant morbidity and mortality. Most valve repair and replacement procedures require a thoracotomy, to gain access to the patient's thoracic cavity. Surgical intervention within the heart frequently requires isolation of the heart and coronary blood vessels from the remainder of the arterial system and arrest of cardiac function, using a cardiopulmonary bypass machine. Open chest techniques with large sternum openings are used. Those patients undergoing such techniques often have scarring retraction, tears or fusion of valve leaflets, as well as disorders of the subvalvular apparatus.

Naturally, surgical patients desire operations that are performed with the least amount of intrusion into the body. Recently, a great amount of research has been done to reduce the trauma and risk associated with conventional open heart valve replacement surgery. In particular, the fields of minimally invasive surgery (MIS) and percutaneous surgery have exploded since the early to mid-1990s, with devices now being proposed to enable valve repair without opening the chest cavity, and some without even requiring bypass. Proposed MIS heart valve repair procedures are accomplished via elongated tubes or cannulas introduced through one or more small access incisions in the thorax, with the help of endoscopes and other such visualization techniques. For example, see U.S. Pat. No. 6,602,288 to Cosgrove. Such minimally invasive procedures usually provide speedier recovery for the patient with less pain and bodily trauma, thereby reducing the medical costs and the overall disruption to the life of the patient. A minimally invasive approach also usually results in a smaller incision and, therefore, less scarring, which is an aesthetic advantage attractive to most patients.

The use of a minimally invasive approach, however, introduces new complexities to surgery thus placing a greater burden on the operating surgeon. Most notably, minimally invasive approaches drastically reduce the size of the surgical field available to the surgeon for the manipulation of tissue and for the introduction of necessary surgical instruments, such as cutting devices, clamps, prosthetic holders, and so on. These complexities are especially acute in connection with heart surgery. Unlike common heart surgeries performed using a full medial sternotomy, minimally invasive heart surgery offers a surgical field that may be only as large as a resected intercostal space or a transversely cut and retracted sternum. Consequently, the introduction of tools, such as prosthetic sizing elements, valve holders, annuloplasty ring holders, and other such devices, becomes a great deal more complicated.

What is needed, therefore, are devices and methods for carrying out heart valve repair that reduce the trauma, risks, recovery time and pain that accompany current techniques.

SUMMARY OF THE INVENTION

The present application provides an annuloplasty ring comprising an inner core member extending around the entire periphery of the ring in either a closed or open shape. The inner core member has a majority of its length with a first elastic modulus sufficiently flexible to enable the core member to be compressed from its relaxed ring shape into a narrow shape suitable for passage through a tubular access device. The inner core member further includes a plurality of discrete control points located at spaced apart locations, the control points creating localized regions of higher elastic modulus than the first elastic modulus.

Another aspect of the application is an annuloplasty ring, comprising a flexible core member extending around the entire periphery of the ring in either a closed or open shape, the flexible core member having a first elastic modulus. A plurality of discrete control points are located around the flexible core member at spaced apart locations. The control points create localized regions of higher elastic modulus than the flexible core member and at least one control point is bent to control the shape of the core member.

Another annuloplasty ring disclosed herein includes a flexible braided cable extending around the entire periphery of the ring in either a closed or open shape. A plurality of discrete control points located around the flexible braided cable at spaced apart locations create localized regions of higher elastic modulus than the flexible braided cable. The flexible braided cable preferably comprises a multi-stranded braided cable. In one embodiment, the braided cable comprises strands of at least two different metals braided together.

A still further annuloplasty ring of the present application has an inner core member extending around the entire periphery of the ring in either a closed or open shape. A majority of the length of the inner core member has a first elastic modulus sufficiently flexible to enable the core member to be compressed from its relaxed ring shape into a narrow shape suitable for passage through a tubular access device. The inner core member further includes a plurality of discrete control points located at spaced apart locations, the control points creating localized regions of higher elastic modulus than the first elastic modulus.

The annuloplasty rings disclosed herein may have a flexible core member comprises a multi-stranded braided cable. Desirably, the multi-stranded braided cable has at least seven braided cables in cross-section.

In one embodiment, an annuloplasty rings is shaped for implant at the mitral annulus and has a convex posterior portion and a relatively straight anterior portion, and wherein there are at least three control points. Preferably, there is a control point centered on a minor axis of the ring in the posterior portion.

In an annuloplasty ring shaped for implant at the tricuspid annulus, there are at least three control points.

The control points may comprise tubular members extending at least 3 mm in length crimped to the flexible core member. Alternatively, the control points each comprises a coiled wire extending at least 3 mm in length and helically wrapped around the flexible core member. Still further, alternative the control points comprise regions of the a flexible braided cable that are welded, soldered, polymer overmolded or adhered to be stiffer than adjacent regions of the flexible braided cable.

In one embodiment a multi-stranded cable replaces solid core wire for both the tricuspid and mitral valves. Cable allows for greater deployment flexibility for minimally-invasive surgical (MIS) implant, while still maintaining the required strength and similar tensile properties of solid-core wire. In addition, selective placement of point-welds or other such control points locally control other parameters such as the amount and direction of displacement as the ring undergoes external loading. Cable with well-placed control points result in a MIS annuloplasty ring with sufficient flexibility in the x-y plane to allow a surgeon to squeeze the ring into a 1 cm×1 cm incision, while maintaining structural rigidity under forces exerted on the implanted ring by the cardiac cycle and allowing for asymmetrical deflection to be designed into the product.

A further understanding of the nature and advantages of the invention will become apparent by reference to the remaining portions of the specification and drawings.

BRIEF DESCRIPTION OF THE DRAWINGS

FIGS. 1A and 1B are plan and elevational views, respectively, of an exemplary inner core member having a braided cable and control points for an open mitral annuloplasty ring;

FIGS. 2A and 2B are plan and elevational views, respectively, of an exemplary inner core member having a braided cable and control points for a closed mitral annuloplasty ring;

FIGS. 3A and 3B are plan and elevational views, respectively, of an exemplary inner core member having a braided cable and control points for a closed asymmetric mitral annuloplasty ring;

FIG. 4A is a partially cutaway plan view of an exemplary closed mitral annuloplasty ring with a core member similar to FIGS. 2A and 2B, while FIG. 4B is an isolated view of the cable used in the core member and FIG. 4C is a cross-section though the ring at a control point;

FIG. 5 is a schematic view of the core member from the ring of FIG. 4A squeezed into an elongated shape and passed through a delivery tube;

FIGS. 9-12 are pairs of drawings illustrating a simulated force application to a mitral annuloplasty ring having varying numbers and locations of control points;

FIGS. 13-16 are pairs of drawings illustrating a simulated force application to a tricuspid annuloplasty ring having varying numbers and locations of control points, namely:

FIG. 13A is a model of an open or C-shaped tricuspid ring having no control points, while

FIG. 14A is a model of an open or C-shaped tricuspid ring having one control point, while

FIG. 15A is a model of an open or C-shaped tricuspid ring having two control points, while

FIG. 16A is a model of an open or C-shaped tricuspid ring having three control points, while

FIGS. 19A-19C are side, posterior, and top plan views, respectively, of a still further alternative flexible open annuloplasty ring with control points;

FIGS. 20A-20C are side, posterior, and top plan views, respectively, of a still further alternative flexible open annuloplasty ring with control points;

FIGS. 21A-21D are schematic views illustrating a distal end of a tubular delivery system having a guide wire that may be used for implanting an open annuloplasty ring of the present application;

FIGS. 22A-22C are sectional views through the distal end of alternative tubular delivery system having a different guide wire used for implanting an open annuloplasty ring of the present application;

DESCRIPTION OF THE PREFERRED EMBODIMENTS

Figure 6A:
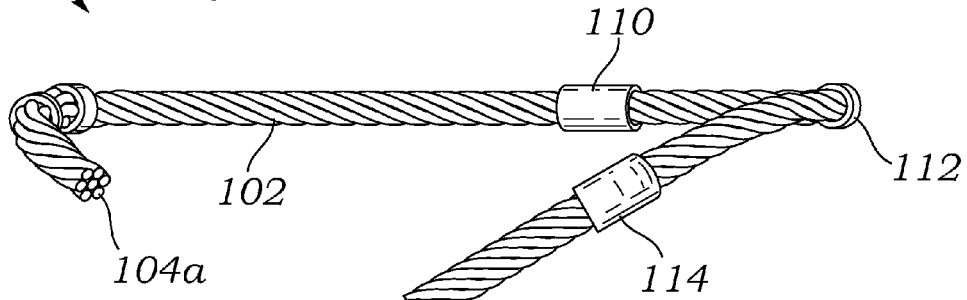
FIGS. 6A and 6B are elevational and plan views, respectively, of an exemplary inner core member having a braided cable and control points for an open tricuspid annuloplasty ring.

The present invention provides a number of different annuloplasty rings or repair segments. It should be understood that the term annuloplasty ring or repair segments refers to any generally elongated structure attachable to the inner native valve annulus and used in annulus repair, whether straight or curved. For example, an annuloplasty ring is conventionally understood to provide either a complete or substantially complete loop sized to correct a misshapen and or dilated native annulus and which is sutured or otherwise attached to the fibrous annulus from which the valve leaflets extend. In many instances, a partial ring or even a straight repair segment may be used around just a portion of the annulus, such as around the posterior edge.

A first embodiment of the present invention is illustrated in FIGS. 1A and 1B in which a core member 20 for a flexible mitral annuloplasty ring defines a posterior portion 22 and an anterior portion 24. Per convention, the core member 20 resembles an open D-shape with the outwardly convex posterior portion 22 and a substantially straight anterior portion 24 extending generally between commissures, or possibly the trigones, of the annulus. An annuloplasty ring that includes the core member 20 may also have a suture-permeable outer covering (not shown), such as a silicone tube surrounding the core member 20 which is then surrounded by a fabric tube. The suture-permeable covering provides anchoring material through which to pass sutures for attaching the annuloplasty ring to the annulus. The traditional construction is seen in FIGS. 4A and 4C. The present application contemplates a number of embodiments of core members 20, and it will be understood that any outer coverings known may be used.

A word about the mitral valve anatomy is necessary. The mitral valve includes a relatively large posterior leaflet and smaller anterior leaflet, both of which attach at their outer peripheries at the mitral annulus. The conventional representation of these two leaflets shows the posterior leaflet below the anterior leaflet, with their line of coaptation, or contact in the flow stream, as a smile-shaped curve. The mitral valve commissures define distinct areas where the anterior and posterior leaflets come together at their insertion into the annulus—which can be imagined as the corners of the smile-shaped coaptation line. The anterior portion of the mitral annulus attaches to the fibrous trigones and is generally more developed than the posterior annulus. The right fibrous trigone is a dense junctional area between the mitral, tricuspid, non-coronary cusp of the aortic annuli and the membranous septum. The left fibrous trigone is situated at the junction of both left fibrous borders of the aortic and the mitral valve. Although the trigones and commissures are proximate to each other, they are not at the exact same location.

The exemplary core member 20 comprises a flexible cable 26 having a plurality of discrete control points or members 28-30 thereon. The control points may take a number of configurations, but act to rigidify and define the shape of the core member 20. In the illustrated embodiment, the control points 28-30 comprise tubular sleeves or crimps squeezed onto the flexible cable 26 at select locations. For example, two anterior crimps 28 are provided at approximately the locations at which the commissures of the mitral annulus are located, or in other words at the end boundaries of the anterior aspect or anterior leaflet. The two anterior crimps 28 are curved and preferably metallic so as to be mechanically squeezed and deformed tightly around the cable 26. The cable 26 thus assumes corners at the location of the anterior crimps 28. Likewise, two intermediate crimps 30 help shape the cable 26 into the preferred D-shape. The core member 20 is desirably symmetric about a minor (vertical) axis such that the crimps 28, 30 are located symmetrically across from their counterparts. However, as will be explained, an asymmetric distribution of crimps may also be desired. Finally, the core member 20 has a single posterior crimp 32 in the middle of the posterior portion 22.

The core member 20 includes two free ends 34 separated across the minor axis in the middle of the anterior portion 24. As seen in FIG. 1B, the anterior portion 24 bows upward from a plane in which the posterior portion 22 lies, such that the free ends 34 project upward toward each other. The core member 20 when in its relaxed, unstressed state is shaped the same as a Carpentier-Edwards® Classic® Annuloplasty Ring available from Edwards Lifesciences of Irvine, Calif. As will be clear below, the open nature of the core member 20, and annuloplasty ring formed thereby, permits a surgeon to open the structure up into an elongated strand for delivery through a small tube such as a catheter or cannula.

It should be understood that the core member 20 comprises a substantially elastic construction that permits it to be elongated and stressed from its relaxed shape as shown into a linear configuration for delivery through an access tube. The rings described herein thus have a relaxed or unstressed shape and a stressed delivery shape. The unstressed shape as shown in the drawings generally describes the shape after implant, though external forces from the surrounding annulus may deflect the unstressed shape a little. Desirably there is a balance between permitting the ring to elongate for delivery while at the same time being able to remodel to a certain extent the particular annulus consistent with the relaxed shape. Conventional remodeling rings include a more rigid core, such as solid titanium, while wholly flexible rings are typically formed of silicone, neither of which would be suitable for the present purpose.

A second embodiment of the present invention is illustrated in FIGS. 2A and 2B in which a core member 40 for a flexible mitral annuloplasty ring defines a posterior portion 42 and an anterior portion 44. As before, the core member 40 resembles a D-shape with the outwardly convex posterior portion 42 and a substantially straight anterior portion 44. However, in contrast to FIGS. 1A-1B the core member 40 has a closed peripheral shape. An annuloplasty ring that includes the core member 40 may also have a suture-permeable outer covering (not shown), such as a silicone tube surrounding the core member 40 which is then surrounded by a fabric tube, such as seen in FIGS. 4A and 4C.

The closed mitral core member 40 features the same number and location of control points or members as in the open ring above. Namely, the core member 40 is formed by a braided cable 46 having two symmetric anterior control points 48, two symmetric intermediate control points 50, and a single posterior control point 52 centered on a minor axis of the D-shape. The control points are again illustrated as tubular crimps, though as will be explained below other configurations are possible. FIG. 2B shows the core member 40 in elevational view illustrating an anterior bow 54. The core member 40 when in its relaxed, unstressed state desirably has the same shape as the Carpentier-Edwards® Physio® Annuloplasty Ring available from Edwards Lifesciences.

A still further embodiment of the present invention is shown in FIGS. 3A and 3B. A core member 60 for a flexible mitral annuloplasty ring defines a posterior portion 62 and an anterior portion 64. The core member 60 has a modified D-shape with the outwardly convex posterior portion 62 being pulled in on the right side so as to be asymmetric. As with FIGS. 2A-2B the core member 60 has a closed peripheral shape, but in this embodiment in its unstressed state mimics the shape of the Carpentier-McCarthy-Adams IMR ETlogix™ Annuloplasty Ring, also available from Edwards Lifesciences.

The core member 60 includes four discrete control points or members 68, 70, 72, 74 around the periphery at strategic locations. A first anterior control point 68 is located, when implanted, at one of the commissures of the mitral annulus, and a second anterior control point 70 is at the other commissure. As before, the anterior control points 68, 70 provide some rigidity for the core member 60 and also bend the flexible cable 66 at the opposite anterior corners. A first posterior control point 72 provides rigidity and curves the cable 66 on the left side in plan view, while a second posterior control point 74 is located on the right side in a pulled-in region. FIG. 3B shows the right side of the posterior portion dipping downward at 76, and the control point 74 desirably shapes the cable 66 in this area.

Now with reference to FIG. 4A, an annuloplasty ring 80 comprises a core member that resembles the core member 40 of FIG. 2A, and includes a closed length of braided cable 82 and a plurality, in this case five, discrete control points or members 84. This annuloplasty ring 80 in its relaxed, unstressed state is shaped to mimic the Carpentier-Edwards® Physio II™ Annuloplasty Ring available from Edwards Lifesciences. Although not shown in elevation, the Physio II™ ring has more pronounced upward bows on both the anterior and posterior sides. Also, the larger ring sizes of the Physio II™ ring become less D-shaped and more circular to better correct for pathological changes in mitral annular dimensions seen in larger patients.

FIG. 4B shows a short length of the braided cable 82, which includes seven strands of wire including a central wire and six strands 83 wound helically therearound. This construction is also known in the art as a simple 1×7 cable, having a single winding of seven wires. Other cable constructions are also possible, such as 1×3 or 1×19 simple braids. Preferably, however, the core members will include flexible cables having multi strand braids, such as 7×7, 7×19, 19×7 or even 7×7×7 braided cables. Each of these possible braid constructions is seen in FIGS. 17A-17G, and will be described in greater detail below.

The left side of FIG. 4A shows an outer fabric cover 86 which has been cut away to illustrate a portion of the inner core member. FIG. 4C shows a preferred cross-sectional layout, with the fabric cover 86 surrounding a suture-permeable interface 88, such as a silicone rubber tube. The interface 88 closely surrounds the control point 84, which in the illustrated version is a crimped tube. Inside the crimp 84 is the braided cable 82.

FIG. 5 schematically illustrates the core member of the annuloplasty ring 80 squeezed into an elongated shape to fit within a tubular access device 90. The flexible cable 82 facilitates the conversion from D-shaped to linear so that the ring 80 may be introduced to an implant site through the access device 90. The access device 80 may be a cannula or introducer tube, or other similar expedient.

This delivery method is enabled by the multi-stranded cable 82 which has the flexibility to accommodate large amounts of bending without permanent deformation. However, the disadvantage of cable is that it is not as easy to permanently shape into a ring. This issue is addressed by introducing the "control points" 84 at discrete locations on the cable 82 where a defined bend is desired. Eventually, these control points might be precise spot-welds on the cable ring, but in the illustrated embodiment small steel pins or tubes are crimped or wrapped around a section of cable 82 and bent to the desired curvature.

Figure 6B:
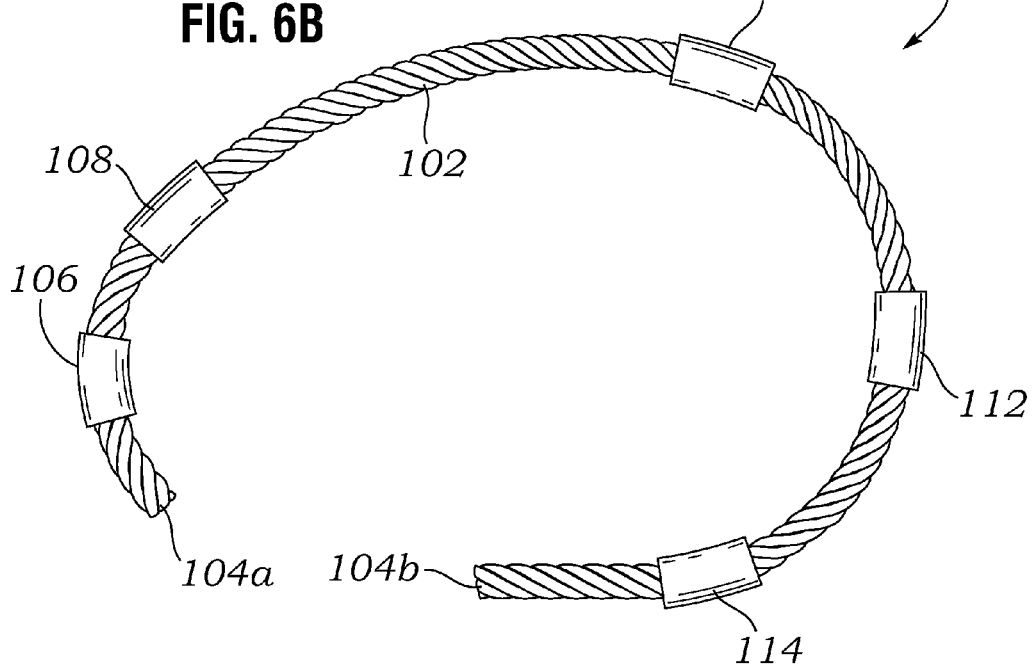

FIGS. 6A and 6B show a still further core member 100 in the shape of a tricuspid annuloplasty ring. As in the earlier embodiments, exterior components such as a silicone interface and fabric cover are not shown to better illustrate the flexible core member 100. The core member 100 when in its relaxed, unstressed configuration is the same shape as an Edwards MC$^3$ Annuloplasty System available from Edwards Lifesciences.

The core member 100 includes a flexible braided cable 102 having two free ends 104a, 104b. A series of discrete control points or members 106, 108, 110, 112, 114 provide rigidity and shape the cable 102. The core member 100 has the classic tricuspid shape in plan view, starting at the first free end 104a and extending in a clockwise direction around a first segment corresponding to the aortic part of the anterior leaflet in which two control members 106, 108 are located. Adjacent to the first segment is a second segment corresponding to the remaining part of the anterior leaflet in which is located a third control member 110, the second segment ending at the postero septal commissure and a fourth control member 112. Finally, a third segment extends from about the fourth control member 112 to the second free end 56b, which is mid-way along the septal leaflet, and includes a fifth control member 114. The nomenclature for these segments is taken from the standard anatomical nomenclature around the tricuspid annulus.

As before, each of the control members 106, 108, 110, 112, 114 provides both rigidity and shape to the core member 100. For instance, the control members 106, 108, 110, 112, 114 all provide the convex curvature in plan view, and also induce the vertical deflections seen in elevational view in FIG. 6A. In the illustrated embodiment, the control members are tubular metallic crimps, but as mentioned above may be provided in different configurations.

Figure 7A:
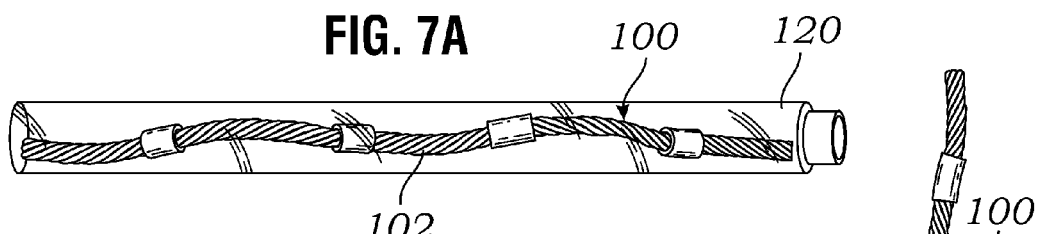
FIGS. 7A and 7B are schematic views of the core member from FIG. 6A opened into an elongated shape and passed through a delivery tube.
Figure 7B:
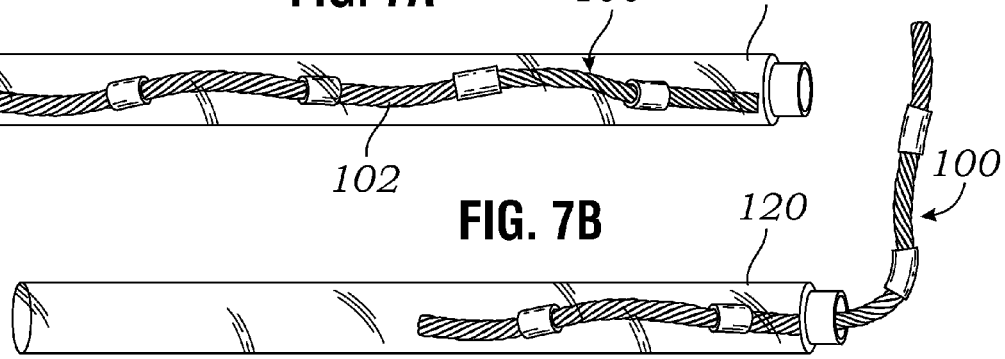

FIGS. 7A and 7B schematically illustrate a technique for delivering an annuloplasty ring having the core member 100 in a minimally-invasive manner. Because of the open nature of the core member 100, with the two free ends 104a, 104b, the ring may be opened up or stretched out relatively straight in a stressed state as seen in FIG. 7A and inserted within a tubular access device 120. The access device 120 may be inserted through an access port in the patient's chest, for example, so that its distal end is positioned at the tricuspid annulus. The core member 100 is seen being expelled from one end of the access device 120 in FIG. 7B and immediately assuming its relaxed unstressed state. In practice, the ring will be expelled from the distal end of the access device 120 so as to assume the unstressed ring shape in approximately the proper implant location, at which time sutures or staples may be used to attach the ring to the annulus. Additional systems for delivering the annuloplasty rings described herein will be presented below.

Figure 8A:
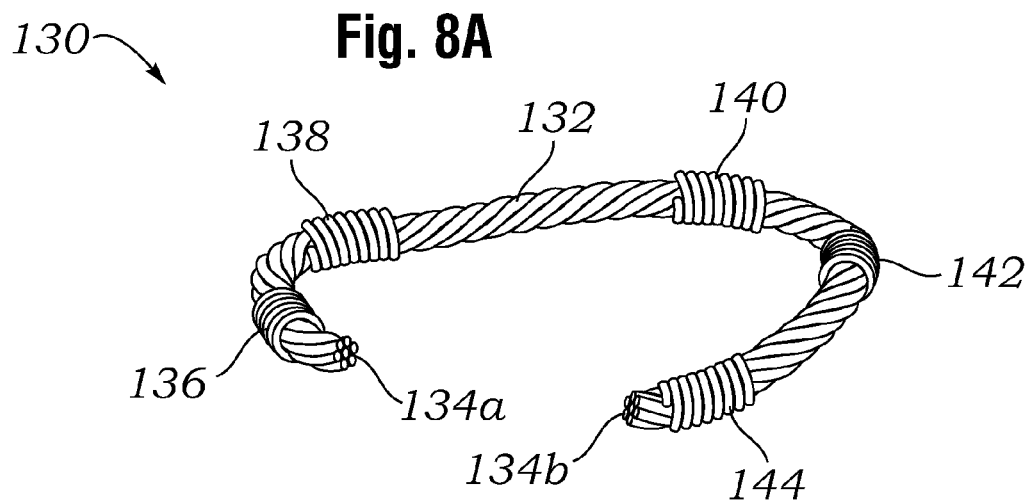
FIGS. 8A-8C are perspective, plan and elevational views, respectively, of an exemplary inner core member having a braided cable and control points for an alternative open tricuspid annuloplasty ring.
Figure 8B:
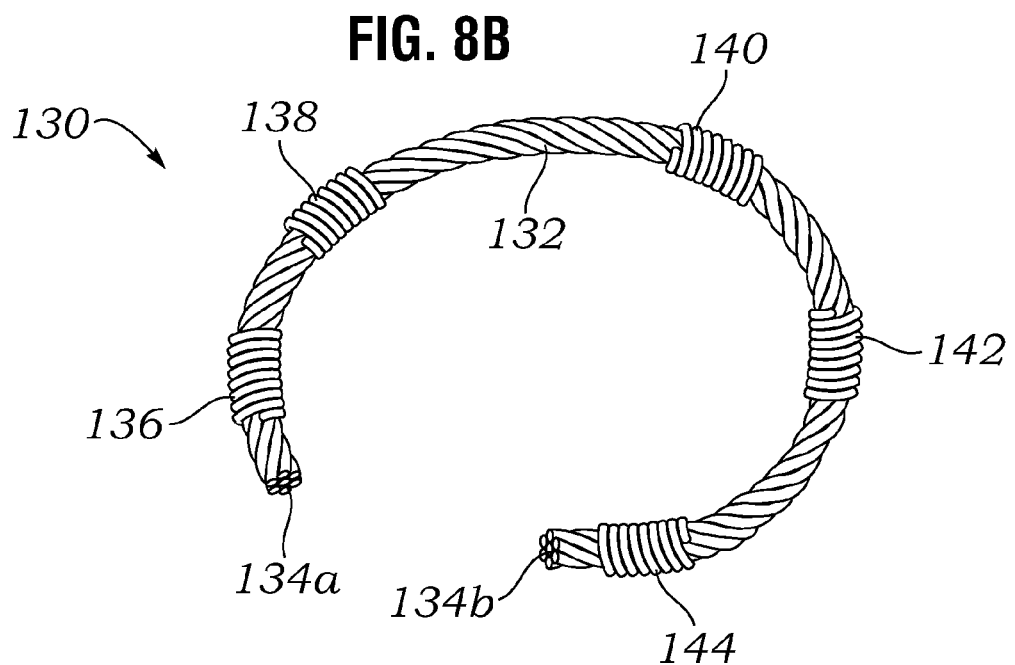
Figure 8C:
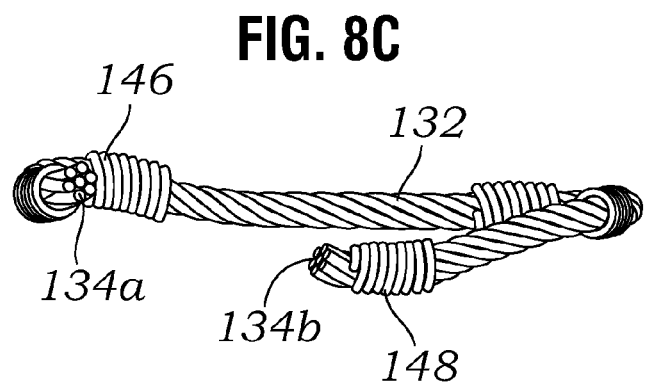
Figure 13A:
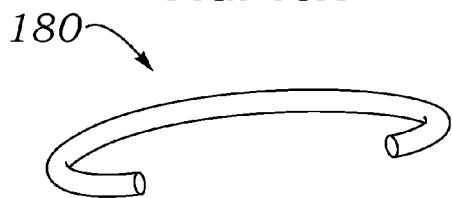
Figure 13B:
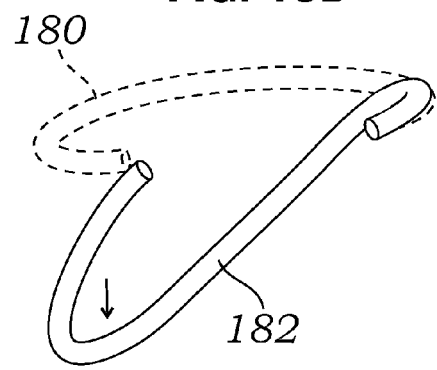
FIG. 13B shows the model under a simulated loaded shape.
Figure 14A:
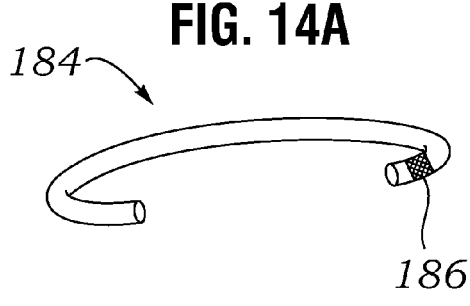
Figure 14B:
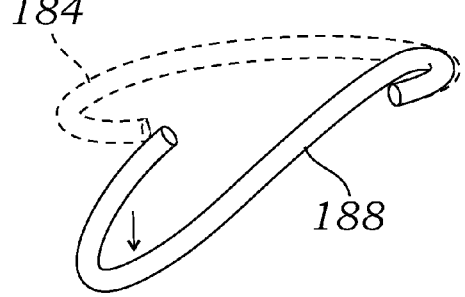
FIG. 14B shows the model under a simulated loaded shape.
Figure 15A:
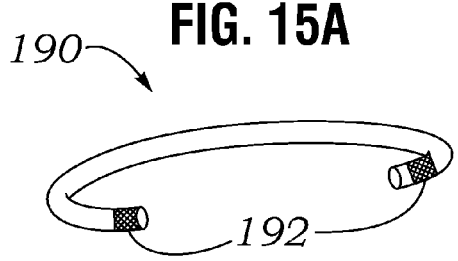
Figure 15B:
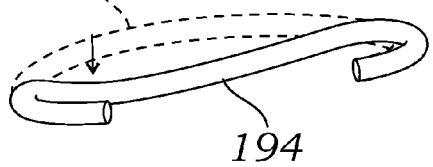
FIG. 15B shows the model under a simulated loaded shape.
Figure 16A:
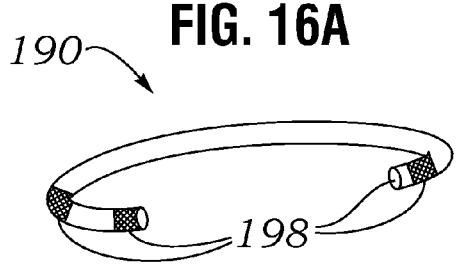
Figure 16B:
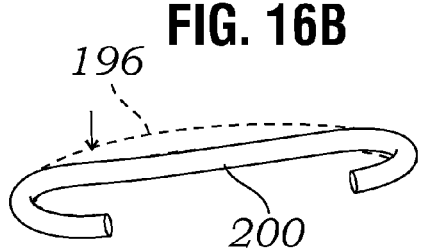
FIG. 16B shows the model under a simulated loaded shape.
Figure 17A:
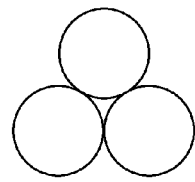
FIGS. 17A-17G show a number of different possible braided cable configurations that may be used.
Figure 17B:
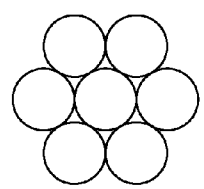
Figure 17C:
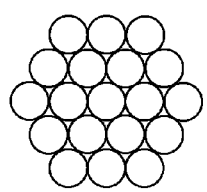
Figure 17D:
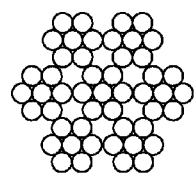
Figure 17E:
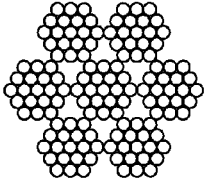
Figure 17F:
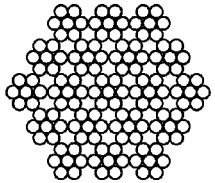
Figure 17G:
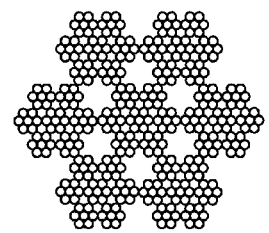

Now with reference to FIGS. 8A-8C, a slightly different core member 130 for a tricuspid annuloplasty ring is shown. The core member 130 includes a braided cable 132 extending from a first free end 132a to a second free end 134b. A number of discrete control points or members 136, 138, 140, 142, 144 are spaced apart along the cable 132. In its relaxed state as shown, the cable 132 is in the shape of a Physio II™ Tricuspid Annuloplasty Ring soon available from Edwards Lifesciences, and includes a waveform shape with up and down regions and two upturned free ends 134a, 134b.

Instead of the tubular crimps for control points as shown above, each control member 136, 138, 140, 142, 144 includes a length of wire or cable wrapped helically around the cable 132. The wrapped wires perform the same function as the crimped metallic tube and provide both rigidity and shape to the core member 130.

The control points or members may be formed in a number of ways other than the crimped tubes and wrapped wires shown above. It is important to understand that the terms "control point" or "control member" refer to short rigid regions (regions of high modulus) on the otherwise relatively flexible (low modulus) ring. The goal of providing a number of discrete rigid regions is to add rigidity and control the final ring shape, which would be difficult with a purely flexible cable. These control points might, for example, be precise spot-welds on the cable ring, or small steel pins crimped or wrapped around a section of cable and bent to the desired curvature. In general, "control points" may be provided by tubular crimps, wound wires, welds, splices, silver solder, heat fused areas, or spot welded regions. Other possibilities include a polymer overmolded around the cable or even certain adhesives that are durable enough to withstand the repetitive flexing motion of the annuloplasty rings.

The concept of a flexible (low modulus) cable combined with carefully selected control points (regions of high modulus) allows designers to "tune" the overall effective modulus of the cable. For example, very flexible cables (e.g. Elgiloy with a moderate strand count and cable diameter of ~0.05 in), could be modified into less flexible ring geometries using careful placement of control points. Once a "target modulus" is predicted for a cable such that appropriate amounts of local displacement will occur along the ring, a variety of cable materials can be selected. Since the use of control points will dictate what the effective modulus is of a particular cable type, material selection need not be constrained by the inherent stiffness of the cable material. A flexible cable, stiffened by control points, provides the ring with sufficient flexibility to compress for delivery through a catheter, while maintaining rigidity in the deployed state. This gives designers valuable freedom, in that materials and cross section can be selected based on cost/familiarity; cable strand count and control points, rather than inherent material properties, are the key design variables.

Furthermore, and as mentioned previously, control points serve to both create the permanent 3D geometry in an otherwise flexible cable, and to locally modify the flexibility of the ring within a given region, allowing asymmetric deflection under the cardiac cycle to be designed into the product. One example of materials is a cable from FWM 1058 Elgiloy, 7×19 strand arrangement, 0.062" diameter, with short tubular Elgiloy crimps.

FIGS. 9-12 and 13-16 illustrate the results of computer simulations of both closed and open rings when certain out-of-plane forces are applied with different control points.

In developing the idea of controlled bending in cables, a number of different computer models have been created and evaluated to simulate the types of forces that these rings will experience inside the heart. In particular, the simulations include a D-ring "control point" model where control points are added and changes in overall displacement are observed, and a C-ring "control point" model where control points are added and changes in overall displacement are observed. It is important to note that these models merely shed light on the concept of "control point-based cable rings" and are not completely representative of what would be seen experimentally. The major goal of these models is to show that cable rings can be manipulated to function similarly to solid-core rings, but still maintain enough flexibility to make minimally invasive (MIS) procedures possible. Also, these models demonstrate that the appropriate placement and number of control points can control both the amount and discrete location of cable displacement.

Parametric Study: Ring Bending Modulus Versus Maximum Displacement

In order to explore the potential of a cable+control points design for MIS annuloplasty rings, we have performed a parametric study of maximum displacement within a ring over a range of ring material modulus values. This model was created using the finite element analysis package COMSOL™ along with a Pro-E geometry of the Edwards generic 196869 "D" ring (mitral valve). Cardiac loads were assumed to be consistent with the forces in the z-axis, described in Table 1.

TABLE 1

Cardiac forces exerted by Mitral valve on D ring

| Location | Force Magnitude |
| --- | --- |
| Anterior | 0.83N |
| Posterior | 0.73N |
| Posterior Commissure | −2.35N |
| Anterior Commissure | −2.64N |

Even though the mitral valve exerts a force in the x-y plane of about 1.88 lbf, this loading condition was neglected in order to simplify the model and focus on the main displacement of the ring in the z-plane. In addition to the four loading conditions seen in Table 1, four locations on the ring were defined as constraints, or areas of zero displacement.

For the parametric model, several modulus values were evaluated for the ring under the same loading conditions. The displacement of the ring was computed for each modulus value and used to create a curve that compares the maximum displacement with the modulus value. A common metric that is useful in describing the elastic behavior of a material is the Elastic Modulus (or Young's Modulus). This value relates the stress applied to a material to the strain that it experiences through the relationship described in Hooke's law. When materials are tested in tension, a material with a lower elastic modulus will experience greater deformation than a material with a higher elastic modulus. However, since these simulations are dealing with bending forces and not tensile forces, we are instead concerned with the bending modulus (also referred to as the flexural modulus) of these cables. Similar to the trend seen with elastic moduli, materials with a lower bending modulus will bend or deflect more than a material with a higher bending modulus. Though there are ways of calculating the bending modulus of a material as a function of its elastic modulus, there is no substitute for experimental measurements of a material's bending modulus. Generally, the bending modulus of a solid-core wire is greater than its elastic modulus, whereas the bending modulus of multi-stranded cable is significantly lower than its elastic modulus.

Figure 26:
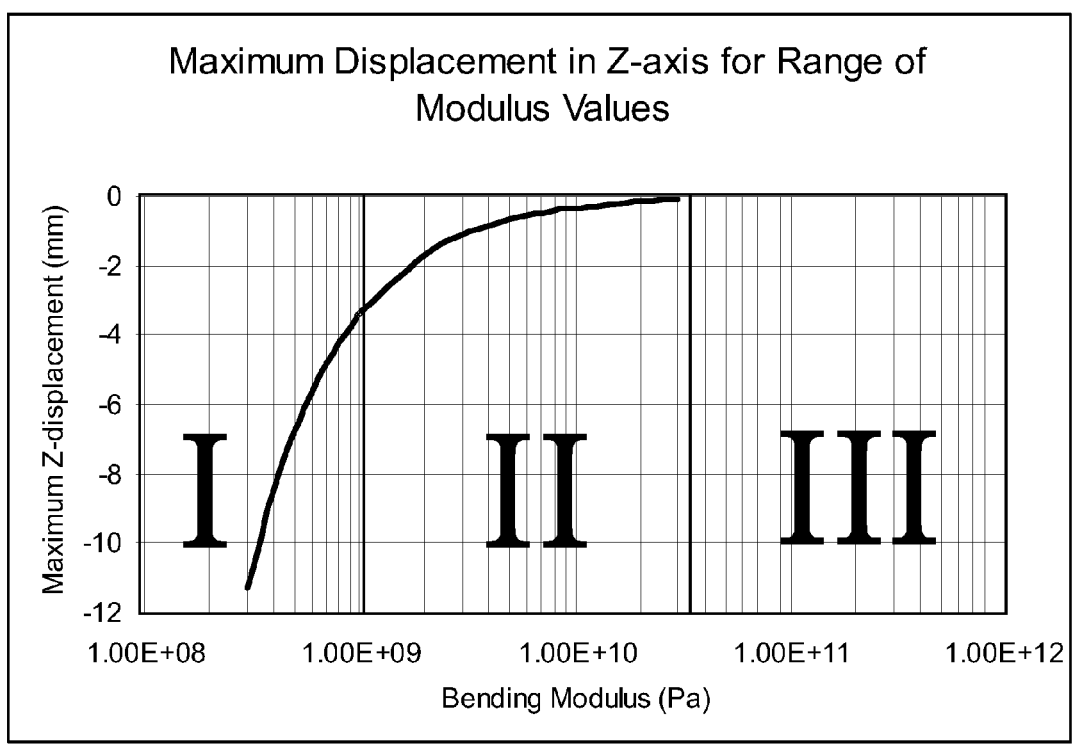
FIG. 26 is a graph showing the displacement of the posterior commissure over a range of modulus values.

The graph of FIG. 26 was created by tracking the displacement of the posterior commissure (found to deflect the most) over a range of modulus values. The relationship between the observable modulus and the maximum displacement can be broken down into three functionally different zones:

Zone 1, referred to as the "pure cable" zone, represents the region of low modulus values characteristic of cable. The specific modulus used in this simulation is the Bending Modulus, which is different than the tensile modulus (known as the Elastic Modulus or Young's Modulus). Though cable and solid-core wire have similar Elastic Modulus values, the Bending Modulus for cable is significantly less than for solid-core wire, (hence its greater flexibility). Under the same applied loads, a cable will deflect more than a solid-core wire, due to its lower bending modulus. In this region, one can change the allowable maximum displacement by selecting cables with different alloys, diameter, or strand count to achieve the desired modulus value. By knowing that lower modulus values correspond to greater maximum displacements, one can select an appropriate cable for a given application.

Zone 3, referred to as the "pure solid-core" zone, represents the region of high modulus values that are characteristic of solid-core wire. When given the same loading conditions as a ring made of cable, a solid-core ring will experience much less overall displacement. In addition, since solid-core wire does not have the inherent flexibility of cable, deformation that occurs will likely be permanent (when compared to cable).

Zone 2, referred to as the "hybrid" zone, represents high potential interest as the intermediate region where rings can be manufactured to take advantage of the overall flexibility of pure cable, but maintain areas of structural rigidity seen in solid-core wire. In this region, low-modulus cables can be "adjusted" to an effective modulus which is greater than their native modulus by introducing control points—point-welds along the ring that can be assumed to have a local modulus that resembles a solid-core wire. Since areas of "pure cable" remain between these control points, the ring will still exhibit much of the same flexibility as pure cable. As more control points are introduced, the ring will exhibit a higher effective modulus until it eventually approximates the modulus of a solid-core wire (this would be the case with an infinite number of control points).

This hybrid region represents the "tunable" range one can utilize by introducing point welds into the cable ring rather than selecting a different material, different thickness, or different strand count. By choosing appropriate locations for these control points, the deformation allowed in each plane can be controlled in addition to the maximum limit.

Control Point Study: D Ring, FIGS. 9-12

In this study, we examined the effects of adding control points on localized displacements, paying attention to the areas of displacement as well as the maximum values. For this simulation, the same geometry and loading conditions described previously for the parametric study were used. Instead of adjusting modulus values throughout the simulation, we selected values representative of a semi-flexible cable and control points and used these values throughout. The cable bending modulus used was 6E8 Pa (about 8.7E4 psi), taken from literature values as a typical modulus near the lower end of the cable range. We used a control point modulus of 2E22 Pa in order to approximate a region with a "near-infinite" bending modulus, as bending within the weld would not be expected if the weld was centered at a distinct point. We also compared the control point model to a similar ring model representing solid-core wire with no control points with a bending modulus of 1.027E10, an order of magnitude less than the elastic modulus for commercially pure titanium (FWM product info).

So, for example, FIG. 9A shows the relaxed shape of a flexible ring 150 having no control points, and FIG. 9B shows the ring shape 12 after having been subjected to the three vertical force arrows shown. FIG. 10A is a ring 154 with two control points 156, and FIG. 10B is the shape 158 after loading with the three vertical forces. FIGS. 11 and 12 continue the progression with more control points 162, 168, and the resulting shapes under load are seen decreasing in FIGS. 11B and 12B. The most obvious trend throughout this study is that as more control points are added, the overall displacement of the ring decreases. Localized displacement tends to decrease the most around areas where control points are added as seen between FIGS. 10B and 11B. Since adding more control points will inherently form a ring that is more representative of a solid-core ring, we expect that overall displacement will decrease for each additional control point added. The important message to take away here is that, by controlling the placement and amount of control points, one can design a cable ring that has regions of controlled displacement. The control points are analogous to points on a spline curve, where each point controls how the line curves.

Control Point Study: C Ring, FIGS. 13-16

FIGS. 13-16 show open or C-shaped tricuspid rings having none, one 186, two 192, and three 198 control points. The corresponding simulated loaded shapes are seen in FIGS. 13B, 14B, 15B and 16B.

The C ring displacement model was very similar to the D model previously described, except that a different loading scheme was used. Instead of 4 independent forces acting on the ring, as seen in the previous model, the C ring model only used one force in the z plane. In reality, one would expect to see the two free ends of the C ring exhibit some displacement since they are sutured to the aortic root and thus part of the contracting heart. However, these ends were modeled as constraints to simplify the model and focus primarily on the effects of adding control points to the C ring as it is pulled down on the anterior end, as seen in FIGS. 13B, 14B, 15B and 16B. The force created by the cardiac cycle was represented by a single force pulling the ring down in the negative z-axis from the anterior end. The force magnitude used was 0.6 N, a little more than half of the anterior force created by the mitral valve. The same modulus values described for the D model, for pure cable and for the control point regions, were used for the C model.

The largest different between the D and C ring results is that the C ring approximated zero displacement with only 3 control points whereas the D ring required about 6. The main cause of this difference is the geometry of the two rings, namely that the C ring is constrained near its midpoint and only has one load throughout the entire geometry. Since the D ring model is less constrained than the C ring model, it has more opportunities to distribute the applied loads intro corresponding displacements. However, we still see the same trend, where adding more control points decreases not only the local z-displacements but the overall displacements as well.

FIGS. 17A-17G show a number of different braided wire configurations that may be used. These include: a simple 1×3 cable in FIG. 17A, a simple 1×7 cable in FIG. 17B, and a simple 1×19 cable in FIG. 17C. Multi-stranded cables include multiple braided cables braided with one another, and include: a 7×7 cable in FIG. 17D, a 7×19 cable in FIG. 17E, a 19×7 cable in FIG. 17F, and a 7×7×7 cable in FIG. 17G. Each of these cables comprises many individual strands that are twisted around each other whereas solid-core wire is composed of a single strand. Even though wide ranges of materials and alloys can be used for both, cable is much more versatile than solid-core wire since different alloys can be used for different strands, different strand counts and geometric placements can be used, and different amounts of coiling can be used. This contrasts the basic nature of solid-core wire where only a single alloy can be used. Because of this unique geometry, cables are typically stronger than wire and yet are also more flexible. When pulled in tension from both ends, cable acts similarly to wire since the different strands are all being pulled in the same direction. However, when a cable is bent, the different strands are allowed to slide past each other slightly, which creates spaces for other strands to occupy and thus is much more flexible than a solid-core wire with the same overall diameter. It is this unique property of cable that makes it an attractive alternative to solid-core wire with respect to annuloplasty rings for minimally invasive surgery. More information on medical grade cables is available from Fort Wayne Metals headquartered in Fort Wayne, Ind. In particular, some cables may be coated with inert polymers for greater biocompatibility.

Although the present application contemplates using both simple (i.e., single braided) and multi-stranded (i.e., multiple braids intertwined) cables, multi-stranded cables are believed better suited for the MIS delivery approach. For open rings, simple cables may be easily stretched linearly for passage through an access tube, but once permitted to relax and resume the annuloplasty ring shape, these simple cables may not have the requisite stiffness for annulus remodeling. As such, a greater number of control points would have to be used, which may place undesirable limitations on overall ring performance. Furthermore, simple cables formed into closed rings may not be able to be squeezed into a linear shape without kinking into permanent bends. On the other hand, multi-stranded cables are more flexible in bending due to their generally smaller individual strands and the ability of those strands to slide with respect to one another. Moreover, in open rings multi-stranded cables retain larger stiffness in the plane of the ring to provide good remodeling without an excessive number of control points.

Preliminary Evaluation of Fort Wayne Metals Cable Samples

A. Semi-Quantitative Analysis of Cable Samples

A series of cable samples, representing typical standard products for biomedical applications, was provided by Fort Wayne Metals (FWM). Table 2 summarizes physical properties of the samples. It should be noted that these are not the only materials contemplated, and the list of suitable materials includes alloys of stainless steel, Titanium, Cobalt Chromium, Nitinol (NiTi) and Platinum-Iridium. Further, blends or combinations of these various materials could be utilized to obtain particular performance characteristics. The number of permutations is essentially limitless.

TABLE 2

Cable samples provided by FWM

| Sample | Material | Diameter (in) | Strand Count |
|---|---|---|---|
| 1 | Ti 6Al 4V ELI | 0.0375 | 19 × 7 |
| 2 | Ti 6Al 4V ELI | 0.0423 | 7 × 7 |
| 3 | L-605 | 0.0625 | 19 × 7 |
| 4 | L-605 | 0.080 | 7 × 7 |
| 5 | FWM-1058 | 0.062 | 7 × 19 |
| 6 | 316 LVM | 0.078 | 7 × 7 |
| 7 | 316 LVM | 0.0475 | 1 × 19 |
| 8 | 316 LVM | 0.0425 | 1 × 7 |
| 9 | MP35N | 0.063 | 7 × 7 |
| 10 | FWM-1058 | 0.125 | 7 × 19 |

A preliminary, semi-quantitative analysis was performed on these samples to determine issues with cable material, diameter, and strand count with respect to the control point concept. FIG. 11 illustrates the experimental setup. A minimum bending diameter was determined visually, by bending the cable sample back upon itself until either permanent deformation occurred or cable strands began to separate. At this orientation, measurements were taken by a caliper. The force required to hold this minimum bending diameter was estimated by manually applying the necessary load while the cable was resting on a laboratory scale. Additionally, the cable samples were evaluated for minimum bending diameter with moderate deformation (defined as a ~10 degree bend remaining in the cable after removing load), as well as "robustness", which was based on qualitative observation of how much bending/deformation cables could withstand without suffering permanent damage (kinking, strand separation, or permanent deformation). The results of this preliminary analysis are presented in Table 3.

TABLE 3

Results of semi-quantitative analysis on cable samples provided by FWM.

| Sample | Min Dia (mm) | Force (g) | Robustness | Def. Dia (mm) |
|---|---|---|---|---|
| 1 | 6.9 | 48 | F | 4.8 |
| 2 | 9.5 | 130 | G | 6.5 |
| 3 | 14.9 | 228 | G | 9.4 |
| 4 | 25.4 | 460 | G | 13.7 |
| 5 | 12.1 | 185 | G | 8 |
| 6 | 20.4 | 560 | G | 12 |
| 7 | 16.2 | 480 | F | 10.7 |
| 8 | 22.8 | 580 | P | 20 |
| 9 | 17.6 | 385 | G | 9.9 |
| 10 | 16.5 | 410 | G | 10.5 |

Results in Table 3 may be sorted to identify good (G), acceptable or fair (F), and poor (P) values with respect to the features necessary for use in MIS Annuloplasty Rings. As discussed previously, the ideal characteristic is for a cable to be sufficiently flexible to compress for delivery through a catheter, yet maintain rigidity in the deployed state. Given this, samples that had a minimum bending diameter of <10 mm were considered good, while those with a minimum bending diameter of >20 mm were considered poor. While force to maintain this bending diameter is not a direct measure of cable bending modulus, it is a reasonable indirect measure; for this reason, an arbitrary value of >400 g was considered good, while <200 g was considered poor. One noticeable result was that low-strand-count cables (#7 & #8), were considerably less robust compared to the higher strand count cables.

Among these cable samples, samples 2, 3, 9, & 10 had the best overall relative combination of stiffness, compressibility, and robustness. While it is premature to form specific cable selection recommendations, qualitative observations and this data suggest that a cable diameter of less than 0.08 in, combined with a strand count of 7×7, 7×19, or 19×7, is best suited for the control point concept. Material type is a secondary consideration.

B. Cable Selection Considerations

Preliminary evaluation of FWM samples are consistent with the results of computer simulations, with both indicating that a wide variety of cable materials could be used for annuloplasty ring applications. Section I.D. discussed "tuning" the overall effective modulus of the cable through carefully selected control points. Since the use of control points will dictate the effective modulus of a given cable type, material selection is not constrained by the inherent stiffness of the cable material. A likely cable selection strategy is to:

Select material based on availability/familiarity.

Select cable diameter to be similar in diameter to current "solid-core" rings.

Select a standard, off-the-shelf cable, with moderate strand count and low bending modulus, to achieve maximum compression for delivery through catheter.

Add control points necessary to form cable into required three-dimensional geometry.

Add additional control points and/or increase length of control points to achieve required effective modulus and desired local maximum displacements along ring.

Iterate with greater strand count if local maximum displacements are too great.

Thus a flexible cable, stiffened by control points, provides the ring with sufficient flexibility to compress for delivery through a catheter, while maintaining rigidity in the deployed state. Prototypes have been constructed employing this strategy (low modulus+sufficient control points to stiffen the ring). It is also possible to combine multiple cable types to achieve the combination of high bending for deployment as well as high post-deployed stiffness.

Figure 18A:
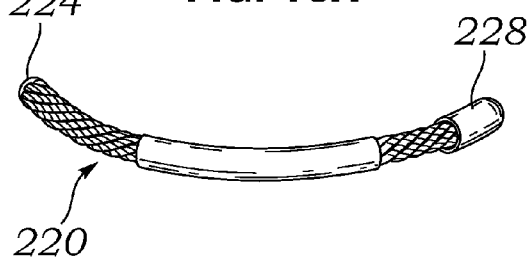
FIGS. 18A-18C are side, posterior, and top plan views, respectively, of a still further alternative flexible open annuloplasty ring with control points.
Figure 18B:
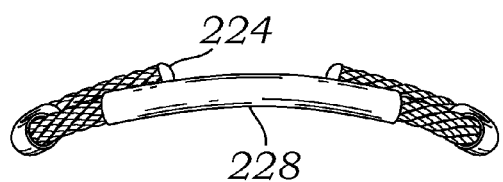
Figure 18C:
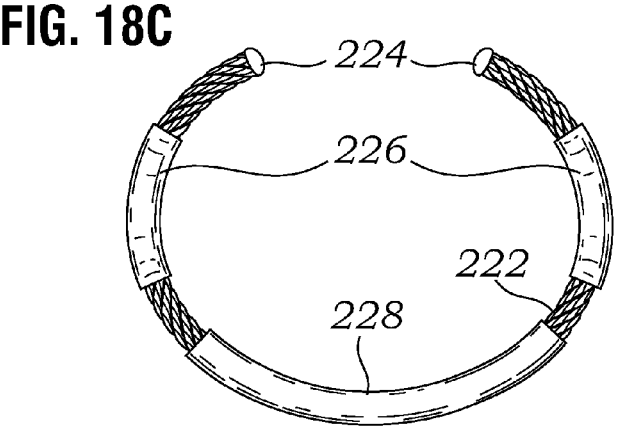

FIGS. 18A-18C are side, posterior, and top plan views, respectively, of an alternative flexible open mitral annuloplasty ring 220 with control points. The annuloplasty ring 220 includes a flexible multi-stranded cable 222 having two free ends 224. In the illustrated embodiment the free ends 224 have been capped or rounded with solder, for example. Two side control points 226 and a single posterior control point 228 provide stiffness and shape to the ring 220. The control points 226, 228 are shown as crimps, though as mentioned other constructions are possible.

The control points 226, 228 of the annuloplasty ring 220 are somewhat longer than previously illustrated. This enhanced the stiffness and shaping ability of each control point, though the ring 220 cannot be straightened quite as much as the rings with shorter control points. The length of the control points in any of the rings described herein may range from between about 3-50 mm, with a preferred range of between about 10-30 mm.

FIGS. 19A-19C are side, posterior, and top plan views, respectively, of a still further alternative flexible open annuloplasty ring 230. As with the previous ring 220, the annuloplasty ring 230 includes a flexible multi-stranded cable 232 having two free ends 234 that have again been capped or rounded with solder, for example. Also, two side control points 236 and a single posterior control point 238 provide stiffness and shape to the ring 230. The control point 238 is slightly shorter than the control point 228 in FIGS. 18A-18C, which renders the ring 230 more flexible than the ring 220.

Finally, FIGS. 20A-20C illustrate another flexible open annuloplasty ring 240 having a flexible multi-stranded cable 242 and free ends 244. This ring 240 includes two side control points 246 as before, but instead of one, two posterior control points 248. The separation of the two posterior control points 248 leaves a length 250 of cable 242 along the minor axis of the ring, which may be desirable as a flex point.

As mentioned above with respect to FIGS. 7A and 7B, one advantage of the flexible annuloplasty rings described herein is their ability to elongate and be delivered through a catheter, or access tube. Current annuloplasty ring on the market are made of a single solid wire or laminated strips formed into the desired three-dimensional C or D geometry. One major limitation of using solid-core wire is that these types of rings cannot easily be manipulated. For example, a surgeon would not be able to squeeze a D-shaped solid ring to the point where two sides meet for insertion through a small (less-invasive) incision. In order to perform less invasive procedures, these rings must eventually have the ability to be inserted through smaller and smaller openings, and ideally being able to deploy through an 18 French catheter. Typically such a catheter for a minimally-invasive surgery will be relatively short so as to be able to reach from outside the patient's chest through the left atrium to the mitral valve, or via the right atrium to the tricuspid valve. The multi-stranded cable rings desirably provide the same functionality as the previous solid-core rings, but can also be manipulated in a way that would enable such less invasive surgical procedures.

In an alternative to the delivery system shown in FIGS. 7A and 7B, FIGS. 21A-21D illustrate a distal end of an exemplary tubular delivery system 300 in which an open annuloplasty ring 302 of the present application passes through an access tube 304, such as a catheter. A guide wire 306 connects to a distal tip 308 of the annuloplasty ring 302 and when pulled (or held in place while the ring is pushed) deflects the distal tip as it emerges from the tube 304. As explained above, the annuloplasty ring 302 has resiliency and ultimately tends towards its relaxed shape as seen at 310 in FIG. 21D, even in the absence of a guide wire. However, the guide wire 306 acts as a positioner to guide the distal tip 308 in a particular direction. In this way, the surgeon can orient the final relaxed form of the annuloplasty ring 310 in the annulus plane. Once the annuloplasty ring 302 has been sutured to the annulus, the surgeon detaches the guide wire 306 and removes it in conjunction with the access tube 304. Although not shown, a pusher is typically used to urge the annuloplasty ring 302 from the distal end of the tube 304.

In an alternative delivery system 320 of FIGS. 22A-22C, an open annuloplasty ring 322 emerges from the distal end of an access tube 324. Again, a guide wire 326 attaches to a distal tip 320 of the annuloplasty ring 322 and directs the distal tip in a particular direction when relatively held or pulled. In addition, the guide wire 326 passes through a midportion 330 of the ring 322 so as to deflect the distal tip 328 to a greater extent (smaller bend radius) than the system of FIGS. 22A-22C. Ultimately, the ring assumes its relaxed shape 332 as seen in FIG. 22C when it emerges completely from the tube 324. Instead of passing through the midportion 330 of the ring 322, the guide wire 326 may be constrained up to that location by a secondary tube (not shown) or other such structure such that the point from which it applies tension to the distal tip 328 is located at the midportion of the ring. Also, the point at which the guide wire 326 applies tension to the distal tip 320 can be adjustable, such as by shifting the position of the secondary tube.

Figure 23A:
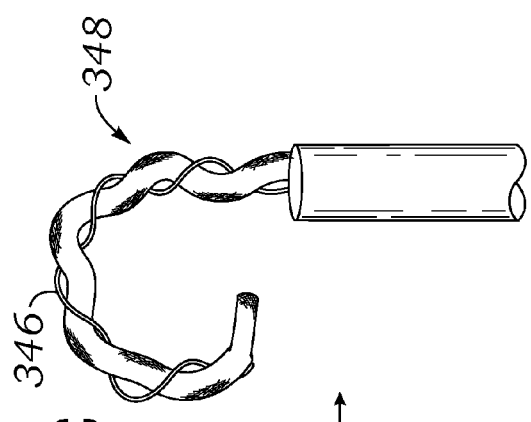
FIGS. 23A-23C are schematic views of the distal end of a tubular delivery system having a corkscrew-shaped guide wire for deploying an open annuloplasty ring of the present application.
Figure 23B:
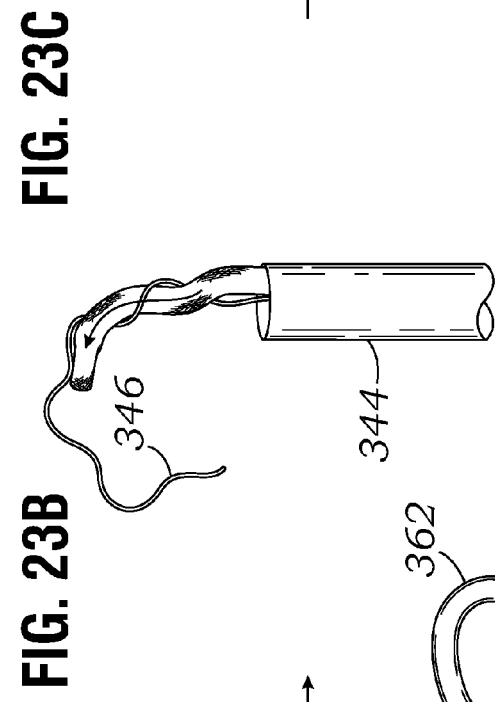
Figure 23C:
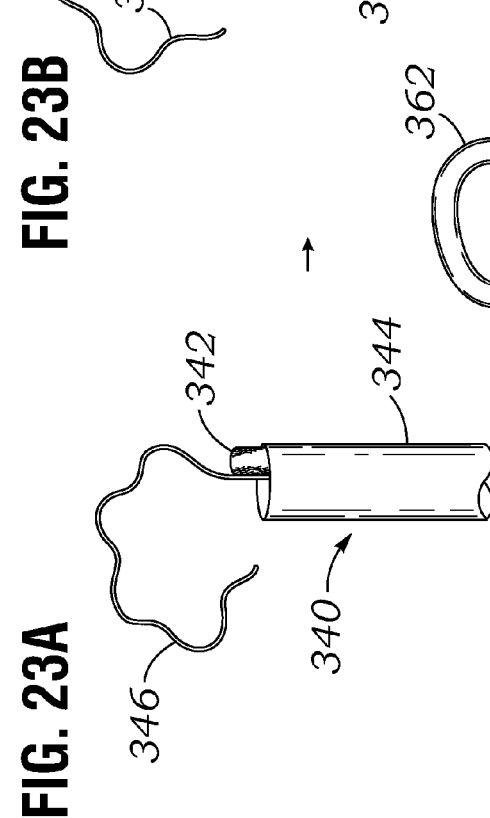

FIGS. 23A-23C illustrate a still further alternative tubular delivery system 340 for deploying an open annuloplasty ring 342 from within a tube 344. In this embodiment, a corkscrew-shaped guide wire 346 is initially position within the tube 344, and then a short length is expelled from the distal tip as seen in FIG. 23A. The guide wire 346 has a helical, corkscrew waveform which mirrors the 3-D contour of the annuloplasty ring 342. As the ring for 342 is pushed and rotated from within the tube 344, it coils around the guide wire 346. The curvature of the guide wire 346 positions the annuloplasty ring 342 as it deploys. Once the ring 342 has been fully deployed around the guide wire 346, it is sutured into the annulus and the guide wire and access tube 344 are removed from the implantation site.

Figure 24:
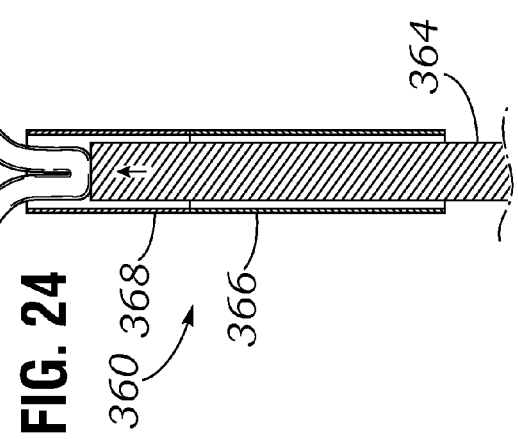
FIG. 24 is a partial sectional view of a still further alternative annuloplasty ring delivery system having a two-part delivery tube and a pusher.

FIG. 24 is a partial sectional view of a still further alternative annuloplasty ring delivery system 360 wherein a closed annuloplasty ring 362 is expelled by a pusher 364 from a two-part delivery tube 366, 368. In this embodiment, a proximal portion 366 of the delivery tube may be somewhat flexible to enable a certain amount of bending during delivery to the implantation site. However, the distal portion 368 is somewhat more rigid so as to support loads imparted on the inner lumen due to compression of the annuloplasty ring 362 and friction during deployment. The two tubular portions 366, 368 may be formed of different polymer materials that are heat bonded together at their junction, or the rigid distal portion 368 may be metallic. Those of skill in the art will understand that a variety of materials and junctions are possible.

Figure 25:
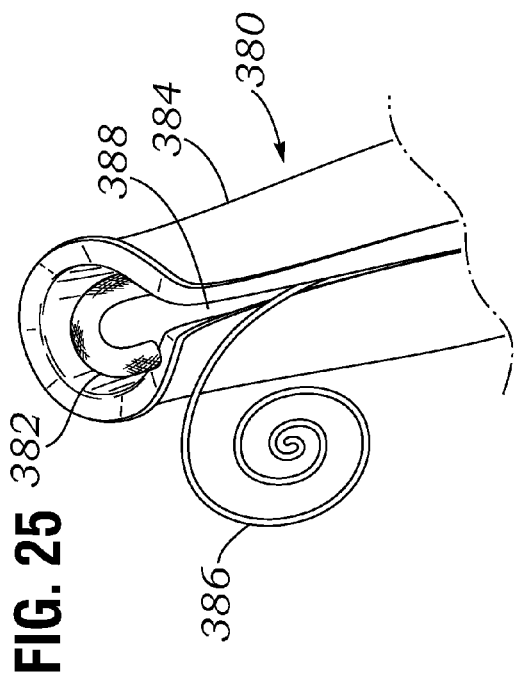
FIG. 25 is a schematic view of the distal end of an alternative tubular delivery system in which an annuloplasty ring of the present application is deployed by peeling away one side of a delivery tube.

Finally, FIG. 25 is a schematic view of the distal end of an alternative tubular delivery system 380 in which an annuloplasty 382 of the present application is deployed by peeling away one side of a delivery tube 384. For instance, a thin filament or ripcord 386 may be provided in the side of the delivery tube 384 which can be peeled away, thus forming an axial opening 388. Because of the resiliency of the annuloplasty ring 382, it eventually expands from its elongated delivery shape into its relaxed final ring shape. One advantage of this delivery system 380 is that they are no frictional pushing or sliding forces resulting from relative motion of the ring and catheter during deployment, as with the earlier embodiments, and thus the end of the access tube 384 need not be so rigid.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An annuloplasty ring adapted for implantation at a native heart valve annulus, consisting essentially of:
   a flexible core member comprising a multi-stranded braided cable formed of multiple metallic wire strands wound into multi-strand braids with the multi-strand braids being braided into the multi-stranded braided cable and having elastic properties with a first elastic modulus and a relaxed shape that forms an open ring with two free ends separated across a gap, the relaxed shape defining a peripheral shape of the ring sized to extend around and be in contact with an endocardial surface of the native heart valve annulus and the elastic properties of the braided cable being sufficient to provide remodeling to the annulus when implanted; and
   an outer covering of suture-permeable material closely encasing the flexible core member.

2. The annuloplasty ring of claim 1, wherein the multi-stranded braided cable has at least seven multi-strand braids in cross-section.

3. The annuloplasty ring of claim 2, wherein the multi-stranded braided cable has a 7×7 cross-sectional braid pattern.

4. The annuloplasty ring of claim 2, wherein the multi-stranded braided cable has a 7×19 cross-sectional braid pattern.

5. The annuloplasty ring of claim 2, wherein the multi-stranded braided cable has a 19×7 cross-sectional braid pattern.

6. The annuloplasty ring of claim 2, wherein the multi-stranded braided cable has a 7×7×7 cross-sectional braid pattern.

7. The annuloplasty ring of claim 1, wherein the multi-stranded braided cable comprises strands of at least two different metals braided together.

8. The annuloplasty ring of claim 1, wherein the multi-stranded braided cable has sufficient flexibility to enable it to be manipulated into an elongated shape to fit within a tubular access device, while the elastic properties cause a return to the relaxed shape when expelled from the tubular access device.

9. The annuloplasty ring of claim 1, wherein the multi-stranded braided cable has sufficient flexibility to enable a bend diameter of <10 mm without permanent deformation.

10. The annuloplasty ring of claim 1, wherein the multi-stranded braided cable is formed of a Cobalt Chromium alloy of minimum bending diameter of <10 mm.

11. The annuloplasty ring of claim 1, wherein individual strands of the multi-stranded braided cable are coated with inert polymers.

12. The annuloplasty ring of claim 1, wherein the multi-stranded braided cable has a diameter of less than 2.03 mm (0.08 in).

13. The annuloplasty ring of claim 1, wherein the suture-permeable outer covering comprises a silicone tube closely encasing the core member and a fabric cover surrounding the silicone tube.

14. The annuloplasty ring of claim 13, wherein the two free ends of the flexible core member are capped.

15. The annuloplasty ring of claim 1, further including at least one point-weld on the flexible core member to locally influence the amount and direction of displacement as the ring undergoes external loading.

16. The annuloplasty ring of claim 1, further including at least one discrete control point located on the flexible core member creating a localized region of higher elastic modulus than the flexible core member.

17. The annuloplasty ring of claim 16, wherein at least one control point is bent to control the shape of the core member.

18. The annuloplasty ring of claim 17, wherein the annuloplasty ring is shaped for implant at the mitral annulus and has a convex posterior portion and a relatively straight anterior portion, and wherein there are at least three control points that control the shape.

19. The annuloplasty ring of claim 18, wherein there is a control point centered on a minor axis of the ring in the posterior portion.

20. The annuloplasty ring of claim 17, wherein the annuloplasty ring is shaped for implant at the tricuspid annulus and there are at least three control points that control the shape.

21. The annuloplasty ring of claim 16, wherein the control point comprises a tubular member extending at least 3 mm in length crimped to the flexible core member.

22. The annuloplasty ring of claim 16, wherein the control point comprises a coiled wire extending at least 3 mm in length and helically wrapped around the flexible core member.

* * * * *